(12) United States Patent
Zenou et al.

(10) Patent No.: US 9,718,022 B2
(45) Date of Patent: Aug. 1, 2017

(54) DEVICE FOR PRODUCING PURIFIED OXYGEN

(71) Applicant: ZENOU Bernard, Le Raincy (FR)

(72) Inventors: Bernard Zenou, Le Raincy (FR); Laurent Zenou, Levallois-Perret (FR)

(73) Assignee: Bernard Zenou, Le Raince (FR)

( * ) Notice: Subject to any disclaimer, the term of this patent is extended or adjusted under 35 U.S.C. 154(b) by 0 days.

(21) Appl. No.: 14/933,721

(22) Filed: Nov. 5, 2015

(65) Prior Publication Data

US 2016/0129387 A1    May 12, 2016

(30) Foreign Application Priority Data

Nov. 7, 2014 (FR) ..................... 14 60810

(51) Int. Cl.
| | | |
|---|---|---|
| *B01D 53/047* | (2006.01) | |
| *C01B 13/02* | (2006.01) | |
| *B01D 53/053* | (2006.01) | |
| *A61M 16/10* | (2006.01) | |

(52) U.S. Cl.
CPC ........ *B01D 53/047* (2013.01); *C01B 13/0259* (2013.01); *A61M 2016/1025* (2013.01); *B01D 53/053* (2013.01); *B01D 2256/12* (2013.01); *B01D 2257/11* (2013.01); *B01D 2257/40* (2013.01); *B01D 2259/401* (2013.01); *B01D 2259/402* (2013.01); *B01D 2259/40007* (2013.01); *B01D 2259/40009* (2013.01); *B01D 2259/40043* (2013.01); *B01D 2259/40062* (2013.01)

(58) Field of Classification Search
CPC ......... A61M 2016/1025; B01D 53/047; B01D 53/053; B01D 2256/12; B01D 2257/11; B01D 2257/40; B01D 2259/40007; B01D 2259/40009; B01D 2259/40062; B01D 2259/40043; B01D 2259/401; B01D 2259/402; C01B 13/0259
USPC ..... 95/130, 138; 96/109–111, 113, 116, 121, 96/132
See application file for complete search history.

(56) References Cited

U.S. PATENT DOCUMENTS

| | | | | |
|---|---|---|---|---|
| 4,566,881 A | * | 1/1986 | Richter | .............. B01D 53/0476 95/122 |
| 4,661,125 A | * | 4/1987 | Haruna | .............. B01D 53/0473 95/102 |
| 4,869,733 A | | 9/1989 | Stanford | |

(Continued)

FOREIGN PATENT DOCUMENTS

JP        2013052021      3/2013

OTHER PUBLICATIONS

Search Report dated 2015.

*Primary Examiner* — Frank Lawrence
(74) *Attorney, Agent, or Firm* — Ipsilon USA, LLP

(57) ABSTRACT

A device for producing purified oxygen, has a feed (1, 1') of a mixture of oxygen and argon, and has at least one bed (2, 2A, 2B) of oxygen adsorption material, a purge (3, 3') for discharging the separated argon and a circuit (4, 4') for injecting a portion of the purified oxygen produced, into the feed (1, 1'). The device has a programmable logic controller (PLC) for treating the degree of purity and/or the production flow rate that can be set by the user and a control of said purge (3, 3') as a function of the degree of purity of the purified oxygen and/or of the production flow rate which are desired by the user.

8 Claims, 2 Drawing Sheets

(56) References Cited

U.S. PATENT DOCUMENTS

| | | | | |
|---|---|---|---|---|
| 4,880,443 | A | * | 11/1989 | Miller .................... B01D 53/04 |
| | | | | 95/127 |
| 4,985,052 | A | * | 1/1991 | Haruna .............. B01D 53/0476 |
| | | | | 95/101 |
| 5,137,549 | A | | 8/1992 | Stanford et al. |
| 5,226,933 | A | | 7/1993 | Knaebel et al. |
| 5,529,607 | A | | 6/1996 | Tan |
| 5,917,135 | A | | 6/1999 | Michaels et al. |
| 6,475,265 | B1 | * | 11/2002 | Baksh .................. B01D 53/047 |
| | | | | 95/101 |
| 2006/0162565 | A1 | | 7/2006 | Lee |
| 2011/0209707 | A1 | | 9/2011 | Terhark |

\* cited by examiner

DEVICE FOR PRODUCING PURIFIED OXYGEN

RELATED APPLICATION

This application claims the benefit of priority from French Patent Application No. 14 60810, filed on Nov. 7, 2014, the entirety of which is incorporated by reference.

BACKGROUND

Field of the Invention

The invention relates to a device for producing purified oxygen.

It relates more specifically to a device for producing purified oxygen by the oxygen production process known as PSA (pressure swing adsorption) which consists in separating the nitrogen molecules contained in the air by passing the air into a column or bed containing a molecular sieve, usually of zeolite type, which is a material having the ability to adsorb the nitrogen molecules, by varying the pressure in an adsorption/desorption cycle.

Description of the Related Art

Although being able to be designed with a single bed, this type of device often comprises two beds that work alternately in adsorption/desorption making it possible to produce, in each cycle, a certain volume of oxygen with a concentration of between 90% and 96%, the other constituents being mainly argon and residues of nitrogen.

Usually, the phases of a PSA cycle are pressurization/production/equalization/depressurization/regeneration.

A second stage may be added to such a device in order to obtain a higher purity of oxygen. Its role is to separate the mixture of oxygen, argon, nitrogen residues and several inert gases in order to extract therefrom oxygen having a high purity that may reach 99.5%.

Also operating according to the PSA process, the second stage comprises one or two beds of molecular sieves, for example carbon molecular sieves, which have the property of adsorbing oxygen. The operation consists in passing the gas mixture into the bed and venting to the atmosphere the portion of the as not adsorbed, namely essentially argon and residues of nitrogen.

Such a device is described, in patent document U.S. Pat. No. 5,137,549.

The two-stage oxygen concentrator that is described therein comprises a first separation stage that separates nitrogen, carbon dioxide, and water vapor from the air. The mixture of oxygen and argon produced by this first stage is injected through a feed valve into a second separation stage which comprises two beds of oxygen adsorption material, a purge for discharging the separated argon, this purge being equipped with a purge valve, and a circuit for injecting a portion of the purified oxygen produced, into the feed of a mixture of oxygen and argon at the feed valve.

The control of the purge valve is carried out in a staggered and alternate manner with respect to the control of the feed valve which itself is carried out at the same time as a transfer valve which is opened or closed in order to connect the two beds in series.

Furthermore, this type of two-stage device for producing purified oxygen is intended to produce a highly purified oxygen and these devices are constructed with fixed parameters defined at the design stage.

By way of example, if a first stage can produce oxygen purified to 93% or 95% with a flow rate of the order of 10 $m^3/h$, a second stage may produce oxygen purified to 99%±0.2% with a flow rate of the order of 5 $m^3/h$.

However, it turns out that the requirement of the users may differ as regards the degree of purity of the oxygen and/or as regards the production flow rate of purified oxygen produced. No solution is currently provided in order to meet these different specific needs or in order to optimize the relative performances of purity of the oxygen produced and of production flow rate, during operation.

OBJECTS AND SUMMARY

The invention solves this problem by proposing a device for producing purified oxygen, intended in particular to constitute the second stage of oxygen production apparatus applying the PSA process, which is particularly effective and has a better energy efficiency.

In order to do this, the invention proposes a device for producing purified oxygen, provided with a feed of a mixture of oxygen and argon, and comprising at least one bed of oxygen adsorption material, a purge for discharging the separated argon and a circuit for injecting a portion of the purified oxygen produced, into said feed, characterized in that it comprises a programmable logic controller for treating the degree of purity and/or the production flow rate that can be set by the user and a control of said purge as a function of the degree of purity of the purified oxygen and/or of the production flow rate which are desired by the user.

The device in accordance with the invention allows interactivity with the user via the choice of the oxygen purity which may be made at the man/machine interface.

In automatic mode, the device may automatically adjust its operation, and consequently the degree of oxygen purity, as a function of the oxygen flow rate desired by the user.

Preferably, the control of said purge consists in the actuation thereof at the same time as the injection of purified oxygen, into said feed, with a purge volume and an injection volume that are variable, as a function of the command received from said controller.

The device may comprise an analyser, a flow meter and/or a pressure sensor for the purified oxygen that provide the monitoring of said actuation and are connected to said controller.

It may also comprise correlation tables for the degree of purity, for the flow rate of the purge and for the volume of said purge providing the control of said controller, these correlation tables being previously recorded in the controller.

Preferably, the device comprises two beds of oxygen adsorption material operating in cycles according to the following phases: pressurization, purge/injection, equalization and depressurization.

The invention also relates no apparatus for producing oxygen from air comprising a first stage of separating nitrogen and a second stage of separating argon consisting of a device as specified above.

BRIEF DESCRIPTION OF THE DRAWINGS

The invention is described below in greater detail with the aid of figures representing only preferred embodiments of the invention.

DETAILED DESCRIPTION

Figure 1:
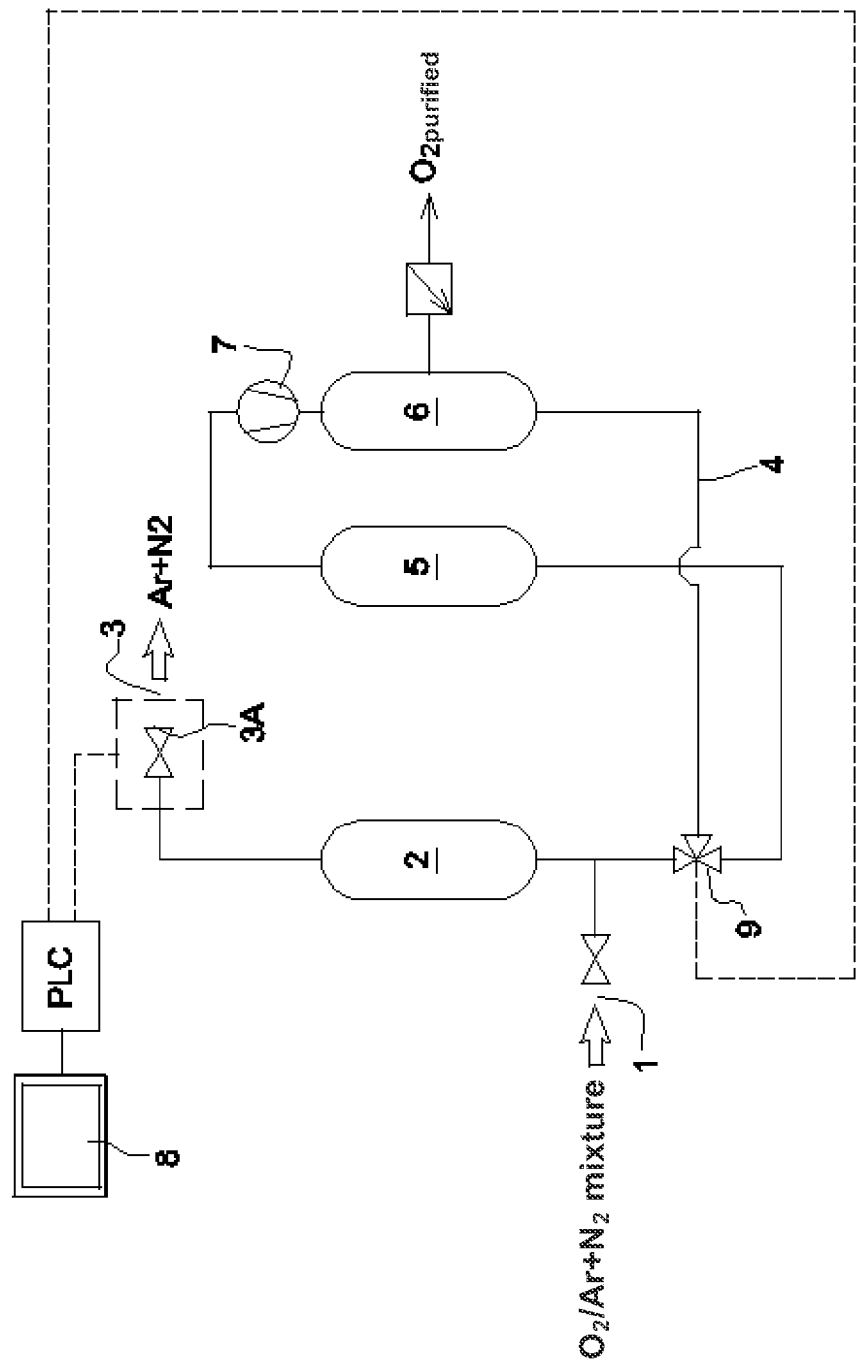
FIG. 1 is a schematic view of a device in accordance with the invention comprising a single oxygen adsorption bed.

As illustrated in FIG. 1, a device for producing purified oxygen is provided with a feed 1 of a mixture of oxygen and argon, and comprises a bed 2 of oxygen adsorption material, a purge 3 for discharging the separated argon and a circuit. 4 for injecting a portion of the purified oxygen produced, into the feed 1.

The mixture of oxygen and argon optionally with a few traces of nitrogen, preferably originating from a first stage of separating nitrogen from air, is fed into the bed 2 containing an oxygen adsorption material which, when the mixture passes through it, retains the oxygen and releases the argon and nitrogen in the upper portion. This argon is discharged to the atmosphere through the purge 3 equipped with a purge valve 3A.

In the bottom portion, via actuation of a three-way valve 9, the purified oxygen is discharged, and is depressurized in a tank 5 then stored in a tank 6 by means of a booster 7. From this tank, purified oxygen at a certain flow rate is produced.

Through a line 4 from this tank, a portion of the purified oxygen may be reinjected into the oxygen and argon feed mixture and treated with this mixture in the pressurized bed 2, via control of the three-way valve 9.

According to the invention, this device comprises a programmable logic controller PLC for treating the degree of purity and/or the production flow rate that can be set by the user, who can enter this data on a monitor 8.

The purge valve 3 is actuated at the same time as this valve 9 for injecting purified oxygen into the mixture of oxygen and argon treated, with a purge volume and an injection volume that are variable, as a function of the command received from said controller.

This PLC controller comprises a control of the purge valve 3A as a function of the degree of purity of the purified oxygen and/or of the flow rate that are desired by the user.

This control may be carried out by means of an analyser, a flow meter and/or a pressure sensor for the purified oxygen chat provide the monitoring of said actuation and are connected to the controller.

It may also be carried out by means of correlation tables of the degree of purity, of the flow rate of the purge and of the volume of the purge providing the control of the controller, these correlation tables being previously recorded in the controller.

Figure 2:
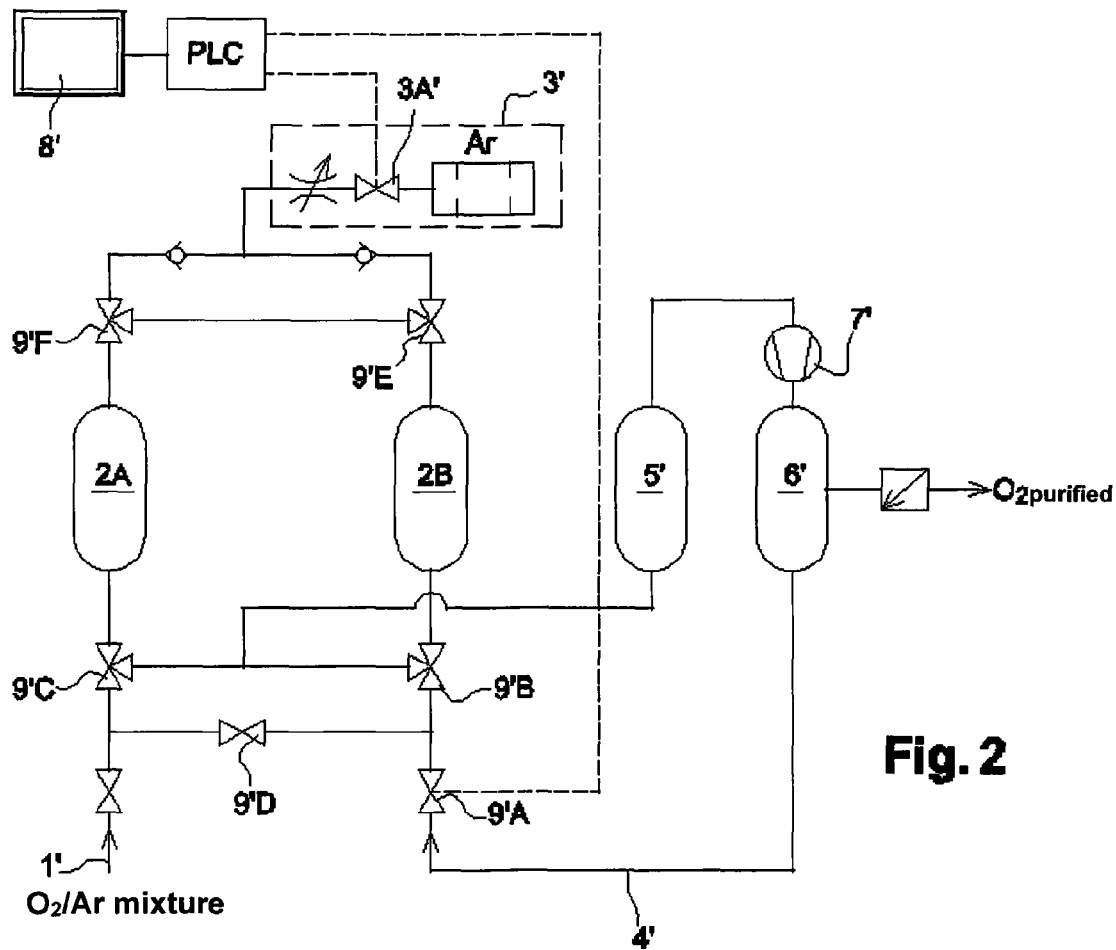
FIG. 2 is a schematic view of a device in accordance with the invention comprising two oxygen adsorption beds.
Figure 3:
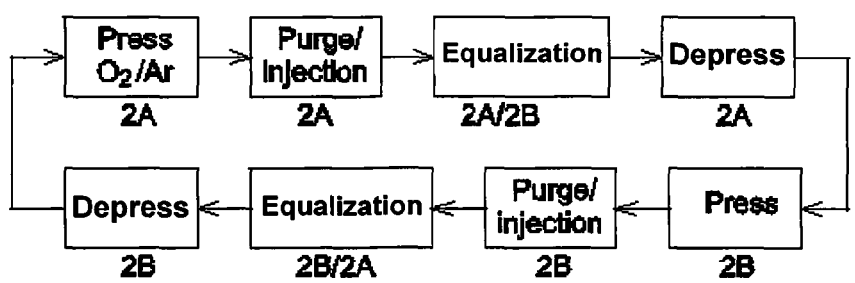
FIG. 3 is a flow diagram of this device.

On the same principle, the invention may be applied to a device for producing oxygen comprising two beds 2A, 2B of oxygen adsorption material as illustrated in FIGS. 2 and 3.

The device for producing purified oxygen is then provided with a feed 1' of a mixture of oxygen and argon, and comprises two beds 2A, 2B of oxygen adsorption material, a purge 3' for discharging the separated argon and a circuit 4' for injecting a portion of the purified oxygen produced, into said feed 1'.

The operation of this device is illustrated in FIG. 3.

The mixture of oxygen and argon optionally with a few traces of nitrogen, preferably originating from a first stage of separating nitrogen from air, is fed into the first pressurized bed 2A containing an oxygen adsorption material which, when the mixture passes through it, retains the oxygen and releases the argon and traces of nitrogen in the upper portion. This argon is discharged to the atmosphere through the purge 3' equipped with a purge valve 3'A.

Via an arrangement of three-way valves 9'B, 9'C, 9'E, 9'F, the oxygen produced is then sent to the second bed 2B for equalization of the pressures of the two beds, depressurization of the first bed 2A and production of purified oxygen, then the second bed 2B is pressurized by supplying the mixture of oxygen and argon and this second bed 2B also contains an oxygen adsorption material which, when the mixture passes through it, retains the oxygen and releases the argon and traces of nitrogen in the upper portion. This argon is discharged to the atmosphere through the purge 3'.

The oxygen produced is then sent to the first bed 2A for equalization of the pressures of the two beds, depressurization of the second bed 2B and production of purified oxygen, and the treatment is continued in alternate cycles.

The purified oxygen produced is depressurized in a tank 5', then stored in a tank 6' by means of a booster 7'. From this tank, purified oxygen at a certain flow rate is produced.

Through a line 4' from this tank, a portion of the purified oxygen may be reinjected by means of valves 9'A, 9'D into the oxygen and argon feed mixture 1' and treated with this mixture in the pressurized beds.

According to the invention, this device comprises a programmable logic controller PLC, which besides controlling the various valves of the device for the production of the purified oxygen production cycles, provides control of the degree of purity and/or of the flow rate that can be set by the user, who can enter this data on a monitor 8'.

The purge valve 3' is actuated at the same time as the purified oxygen is injected by means of the valve 9'A into said feed 1', with a purge volume and an injection of purified oxygen that are variable, as a function of the command received from the controller.

This PLC controller comprises a control of the purge valve 3'A as a function of the degree of purity of the purified oxygen and/or of the flow rate which are desired by the user, as a function of the method of control selected by the user.

As above, this control may be carried out by means of an analyser, a flow meter and/or a pressure sensor for the purified oxygen that provide the monitoring of the actuation and are connected to the controller.

It may also be carried out by means of correlation tables of the degree of purity, of the flow rate of the purge and of the volume of the purge providing the control of the controller, these correlation tables being previously recorded in the controller.

The invention claimed is:

1. Device for producing purified oxygen, comprising:
   a feed of a mixture of oxygen and argon;
   at least one bed of oxygen adsorption material;
   a purge for discharging separated argon; and
   a circuit for injecting a portion of purified oxygen produced into the feed,
   wherein said device further comprises programmable logic controller that controls either one of or both:
      treating a degree of purity of the purified oxygen and/or a production flow rate that can be set by a user; and
      a control of said purge as a function of the degree of purity of the purified oxygen and/or of the production flow rate which are desired by the user.

2. Device according to claim 1, wherein the control of the purge includes the actuation thereof at the same time as the injection of purified oxygen into said feed, with a volume of said purge and an injection of purified oxygen that are variable, as a function of the command received from said controller.

3. Device according to claim 2, wherein said device further comprises an analyser for the purified oxygen that provides the monitoring of said actuation and is connected to said controller.

4. Device according to claim 2, wherein said device further comprises a flow meter for the purified oxygen that provides the monitoring of said actuation and is connected to said controller.

5. Device according to claim 2, wherein said device further comprises a pressure sensor for the purified oxygen that provides the monitoring of said control and is connected to said controller.

6. Device according to claim 2, wherein said device further comprises correlation tables for the degree of purity, for the flow rate of the purge and for the volume of said purge providing the control of said controller, these correlation tables being previously recorded in the controller.

7. Device according to claim 1, wherein said device further comprises two beds of oxygen adsorption material operating in cycles according to the following phases: pressurization, purge/injection, equalization and depressurization.

8. Apparatus for producing oxygen from air comprising: a first stage of separating nitrogen; and a second stage of separating argon having a device according to claim 1.

* * * * *